US00PP12562P2

(12) United States Plant Patent
Meerow

(10) Patent No.: US PP12,562 P2
(45) Date of Patent: Apr. 23, 2002

(54) AMARYLLIS PLANT NAMED 'SAMPA'

(75) Inventor: Alan Meerow, Davie, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 09/396,483

(22) Filed: Sep. 15, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Amaryllis plant named 'Sampa', characterized by its semi-dwarf, compact growth habit; freely flowering habit with three to four scapes per bulb and typically about five to eight open flowers per scape; red purple and white-striped flowers; resistance to Red Scorch Fungus, *Staganospora curtisii* and Leaf Spot, *Cercospora pancratii*; and excellent high temperature tolerance.

1 Drawing Sheet

BACKGROUND OF THE INVENTION

The present invention relates to a new and distinct cultivar of Amaryllis plant, botanically known as Hippeastrum hybrid and referred to by the cultivar name Sampa.

The new cultivar is a product of a planned breeding program conducted by the Inventor in Fort Lauderdale, Fla. The objective of the breeding program is to develop new freely flowering Amaryllis cultivars with novel flower coloration patterns and disease resistance.

The new Amaryllis originated from a cross made by the Inventor in Fort Lauderdale, Fla., of a proprietary selection of the interspecific cross *Hippeastrum papilio*×*Hippeastrum lapacense* identified as H-1-31 (not patented), as the female, or seed, parent with the Hippeastrum hybrid cultivar Apple Blossom (not patented), as the male, or pollen, parent.

The cultivar Sampa was discovered and selected by the Inventor as a flowering plant within the progeny of the stated cross in a controlled environment in Fort Lauderdale, Fla., in 1994. The selection of this new Amaryllis plant was based on its unique flower coloration pattern.

Plants of the new Amaryllis differ from plants of the female parent in the following characteristics:

1. Plants of the new Amaryllis have red purple (57A) and white-striped petals and sepals whereas plants of the female parent have red (45B) with green background-colored petals and sepals.

2. Flowers of plants of the new Amaryllis are much larger than flowers of plants of the female parent.

3. Plants of the new Amaryllis are more freely flowering than plants of the female parent.

4. Flowers of plants of the new Amaryllis are more fragrant than flowers of plants of the female parent.

Plants of the new Amaryllis differ from plants of the male parent in the following characteristics:

1. Plants of the new Amaryllis are much more compact with shorter leaves and scapes than plants of the male parent.

2. Plants of the new Amaryllis have red purple (57A) and white-striped petalls and sepals whereas plants of the male parent have light pink (62B) and white-striped petals and sepals.

3. Plants of the new Amaryllis are more freely flowering with more scapes per plant and more flowers per scape than plants of the male parent.

Asexual reproduction of the new cultivar by twin-scale cuttings taken in a controlled environment in Fort Lauderdale, Fla., has shown that the unique features of this new Amaryllis are stable and reproduced true to type in successive generations.

SUMMARY OF THE INVENTION

The cultivar Sampa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sampa'. These characteristics in combination distinguish 'Sampa' as a new and distinct cultivar:

1. Plants of the new Amaryllis have a semi-dwarf, compact growth habit.

2. Plants of the new Amaryllis are very freely flowering with three to four scapes per bulb and typically about five to eight open flowers per scape.

3. Flowers of plants of the new Amaryllis have red purple and white-striped petals and sepals.

4. Plants of the new Amaryllis are resistant to Red Scorch Fungus, *Staganospora curtisii*, and Leaf Spot Fungus, *Cercospora pancratii.*

5. Plants of the new Amaryllis have exhibited excellent high temperature tolerance.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a close-up view of typical flowers of 'Sampa'. Flower colors in the photograph may appear different from the actual colors due to light reflectance.

DETAILED BOTANICAL DESCRIPTION

The following observations, measurements and values describe plants of the new cultivar that were about two years old from a bulb scale cutting and grown in Fort Lauderdale, Fla., in a polypropylene-covered shadehouse that provided a 50% reduction in ambient light. During the flowering period, day temperatures ranged from 25 to 30° C. and night temperatures ranged from 15 to 18° C.

Color references are made to The Royal Horticultural Society Colour Chart except where general terms of ordinary dictionary significance are used.

Botanical classification: Hippeastrum hybrid cultivar Sampa.

Parentage:

*Female or seed parent.*—Proprietary selection of *Hippeastrum papilio*×*Hippeastrum lapacense* identified as H-1-31, not patented.

*Male or pollen parent.*—Hippeastrum hybrid cultivar Apple Blossom, not patented.

Propagation:

*Type.*—Twin-scale cuttings.

*Time to initiate roots, summer.*—About 25 days at temperatures of 30° C.

*Time to initiate roots, winter.*—About 35 days at temperatures of 22° C.

*Time to develop roots, summer.*—About 60 days at temperatures of 30° C.

*Time to develop roots, winter.*—About 82 days at temperatures of 22° C.

*Rooting description.*—White; numerous; fine and fibrous to moderately thick and fleshy; freely branching.

Plant description:

*Appearance.*—Perennial herbaceous Amaryllis. Upright and clumping growth habit.

*Crop time.*—From bulb scale cuttings, about two years are required to produce a finished, flowering plant in a 15 to 20-cm container.

*Vigor.*—Moderately vigorous.

*Plant height.*—About 45 cm.

*Plant spread.*—About 50 cm.

*Foliage description.*—Arrangement: Distichous, single. Quantity: About five per plant. Length, mature leaves: About 51.5 cm. Width, mature leaves: About 5.75 cm. Shape: Lorate. Apex: Acute. Margin: Entire. Texture: Coarse; glabrous. Color: Young foliage, upper surface: 144A. Young foliage, lower surface: 144B. Mature foliage, upper surface: 137B. Mature foliage, lower surface: 137D.

Flower description:

*Appearance.*—Broad funnel-shaped single flowers arranged in umbels. Corolla and calyx three-parted and fused at the base. Freely flowering, typically about five to eight open flowers per scape and about 15 to 32 flowers and flower buds per bulb. Flowers last about three or four days. Flowers persistent. Flowers held horizontally, perpendicular to scape.

*Flowering response.*—Plants flower continuously in the spring. Plants typically flower about March 1 to March 15 in Fort Lauderdale, Fla.

*Fragrance.*—Moderate.

*Flower diameter.*—About 14 cm.

*Flower depth (height).*—About 15 cm.

*Flower buds.*—Length: About 4 cm. Width: About 1 cm. Shape: Oblanceolate. Color: 57A. Rate of flower bud opening: About 1 to 2 days.

*Petals.*—Length: About 13.5 cm. Width: About 6.5 cm. Shape: Broadly elliptic. Apex: Apiculate. Margin: Entire; undulate. Texture: Smooth; waxy. Color: When opening, upper surface: Red purple, 57A. When opening, lower surface: Red purple, 57A. Fully opened, upper surface: Red purple, 57A with white, close to 155D, striations. Red purple fading to 57D. Fully opened, lower surface: Red purple, 57A, with white, close to 155D, striations. Red purple fading to 57D.

*Sepals.*—Shape: Elliptic. Apex: Apiculate. Margin: Entire; slightly undulate. Color: Upper surface: Red purple, 57A, with white, close to 155D, striations. Red purple fading to 57D. Lower surface: Red purple, 57A, with white, close to 155D, striations. Red purple fading to 57D.

*Scape.*—Length: About 45 cm. Diameter: About 2 cm. Appearance/aspect: Leafless; upright; not fasciated. Strength: Strong. Texture: Smooth. Color: 137D.

*Reproductive organs.*—Androecium: Stamen number: Six. Anther shape: Elliptic. Anther Size: About 3 to 4 mm. Anther color: White. Pollen amount: Moderate. Pollen color: Yellow. Gynoecium: Pistil number: One. Pistil length: About 15 cm. Stigma shape: Trifid. Stigma color: White, close to 155D. Style length: About 15 cm. Style color: White, close to 155D. Ovary color: 141C.

*Seed.*—Seed development has not been observed.

Bulb description:

*Diameter.*—About 7.7 cm.

*Circumference.*—About 23 cm.

*Shape.*—Ovoid.

*Color.*—149A; tunic, 165A.

*Offsets produced per year.*—About three to five offsets per bulb.

Disease resistance: Plants of the new Amaryllis have been shown to be resistant to Red Scorch Fungus, *Staganospora curtisii*, and Leaf Spot, *Cercospora pancratii.*

Heat tolerance: Plants of the new Amaryllis have demonstrated good tolerance to high temperatures about 33 to 35° C.

It is claimed:

1. A new and distinct cultivar of Amaryllis plant named 'Sampa', as illustrated and described.

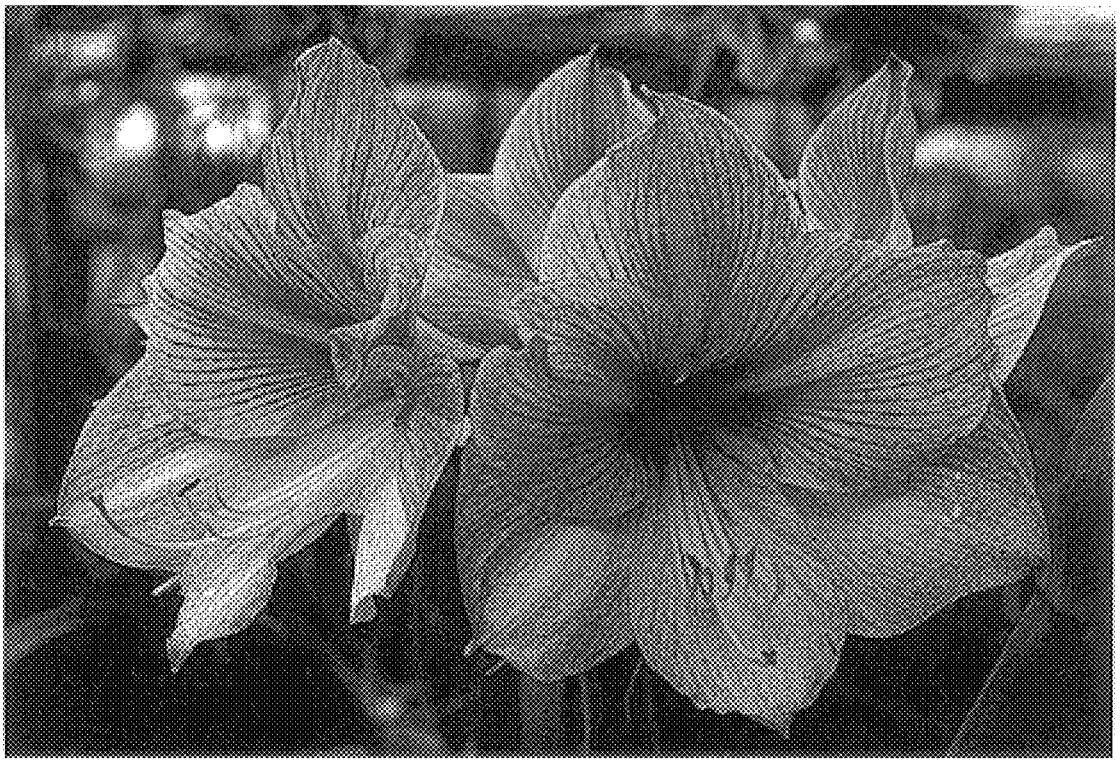

* * * * *